United States Patent
Kennedy et al.

(10) Patent No.: US 9,782,433 B2
(45) Date of Patent: Oct. 10, 2017

(54) CO-NETWORK OF HIGH AND LOW MOLECULAR WEIGHT 3-ARM STAR CYANOACRYLATE-TELECHELIC POLYISOBUTYLENE AND 2-OCTYL CYANOACRYLATE

(71) Applicants: Joseph Kennedy, Akron, OH (US); Istvan Szanka, Balmazujvaros (HU); Amalia Szanka, Budapest (HU)

(72) Inventors: Joseph Kennedy, Akron, OH (US); Istvan Szanka, Balmazujvaros (HU); Amalia Szanka, Budapest (HU)

(73) Assignee: The University of Akron, Akron, OH (US)

( * ) Notice: Subject to any disclaimer, the term of this patent is extended or adjusted under 35 U.S.C. 154(b) by 166 days.

(21) Appl. No.: 14/940,735

(22) Filed: Nov. 13, 2015

(65) Prior Publication Data

US 2017/0136058 A1    May 18, 2017

(51) Int. Cl.
| | |
|---|---|
| *C08F 8/00* | (2006.01) |
| *C08F 8/30* | (2006.01) |
| *A61K 31/74* | (2006.01) |
| *A61K 31/785* | (2006.01) |
| *A61K 31/275* | (2006.01) |

(52) U.S. Cl.
CPC .......... *A61K 31/785* (2013.01); *A61K 31/275* (2013.01)

(58) Field of Classification Search
None
See application file for complete search history.

(56) References Cited

U.S. PATENT DOCUMENTS

| | | | |
|---|---|---|---|
| 7,341,716 B2 | 3/2008 | Porter | |
| 2008/0243082 A1 | 10/2008 | Goodman | |
| 2009/0264566 A1 | 10/2009 | Schambony et al. | |
| 2014/0073743 A1* | 3/2014 | Kennedy | C08F 22/32 525/295 |

* cited by examiner

*Primary Examiner* — Jeffrey T Palenik
(74) *Attorney, Agent, or Firm* — Renner Kenner Grieve Bobak Taylor & Weber (57) ABSTRACT

In one or more embodiments, the present invention relates to a substantially homogeneous miscible liquid adhesive composition comprising a relatively high number average molecular weight ($M_n$=6,000-10,000 g/mole) cyanoacrylate tri-telechelic star polymer having polyisobutylene chains terminated with cyanoacrylate groups (High-Ø(PIB-CA)$_3$); 2-octyl cyanoacrylate (Oct-CA); and a relatively low molecular weight ($M_n$=1,000-4,000 g/mole) cyanoacrylate tri-telechelic star polymer having polyisobutylene chains terminated with cyanoacrylate groups (Low-Ø(PIB-CA)$_3$). The Low-Ø(PIB-CA)$_3$ compatibilizes the High-Ø(PIB-CA)$_3$ and Oct-CA removing the need for a solvent. When the substantially homogeneous miscible liquid adhesive compositions of various embodiments are reacted with a nucleophile, such as water or an initiator, they form a polymer co-network suitable for any of a number of biomedical applications, from wound closure and healing of skin tissue, to sealant for surgical cuts.

23 Claims, 4 Drawing Sheets

CO-NETWORK OF HIGH AND LOW MOLECULAR WEIGHT 3-ARM STAR CYANOACRYLATE-TELECHELIC POLYISOBUTYLENE AND 2-OCTYL CYANOACRYLATE

FIELD OF THE INVENTION

In one or more embodiments, the present invention relates to polyisobutylene-based co-networks polymer co-network useful for wound closure and skin protection made without the use of toxic solvents. In particular, the invention relates to the use of low molecular weight cyanoacrylate tri-telechelic star polymer comprising polyisobutylene to compatibilize high molecular weight cyanoacrylate tri-telechelic star polymer comprising polyisobutylene and poly(2-octyl cyanoacrylate)-polyisobutylene co-networks made thereby.

BACKGROUND OF THE INVENTION

There is a great need in biomedical applications, including orthopedic practice, for sealants or adhesives of wounds and surgical cuts. Such sealants contemplated could range from sealants used for wound healing and wound closure on the skin to sealants used to permanently seal scalpel cuts and puncture wounds made by large bore injection needles in the course of various procedures.

At present, there is no satisfactory orthopedic sealant being used to satisfy the need for closing iatrogenic defects made in the annulus fibrosa during discectomies. This can cause serious problems in that the intervertebral disc may subsequently undergo accelerated degeneration, and the patient may require a spinal fusion some years later. Some implants have been proposed to resolve the issue but these were introduced without biomechanical considerations. Mechanical barriers have been recently proposed but are fundamentally different from an annulus sealant in that it (1) lacks the ability to reconstruct the annulus directly and restore motion, (2) cannot prevent the leakage of smaller particles from within the nucleus pulposus, (3) is more technically difficult to employ, and (4) would carry a significant risk of neurologic injury if extruded into the canal. No long term data is available on these products.

Further, there is also an unmet need for more flexible wound closure adhesives on the surface of the skin. Currently known wound closure adhesives include 2-octyl-cyanoacrylate (Oct-CA), known commercially by the brand name Dermabond®, available from Ethicon US LLC, a Johnson & Johnson company, wherein Dermabond® is a registered trademark of Johnson & Johnson Company, New Brunswick, N.J., and N-butyl-2-cyanoacrylate, known commercially by either Indermil® tissue adhesive, available from Covidien Co., a Henkel company, wherein Indermil® is a registered trademark of Henkel Corporation, Rocky Hill, Conn., or Histoacryl® topical skin adhesive, available from B. Braun Corporation, wherein Histoacryl® is a registered trademark of Aesculap, Inc., Center Valley, Pa. That is, it is well known that these monomers readily polymerize upon exposure to traces of moisture on surfaces such as skin. The CA group in these compounds is highly reactive toward nucleophiles because of the presence of the two highly electron withdrawing substituents (CN— and COO—), so that CA polymerizations are initiated by moisture. For instance, lower alkyl CAs such as methyl cyanoacrylates or ethyl cyanoacrylate (Superglue®) instantaneously polymerize in the presence of surface moisture. The rates of polymerizations are notably lower with the higher alkyl CAs (e.g., Oct-CA) due to the lower molar concentration of the CA groups.

Accordingly, attempts have been made to increase the rate of polymerization of these higher alkyl CAs (e.g., Oct-CA) without introducing any lower alkyl CAs, since the lower alkyl CAs are known to have toxicity concerns and cannot be used inside the body, but yet provide increase flexibility upon polymerization and higher viscosity than is normally available using commercially available wound closures containing 2-octyl-cyanoacrylate (Oct-CA) as the active ingredient. That is, commercial products such as Dermabond® are known to exhibit undesirably low viscosity (i.e., too runny) and to exhibit undesirable stiffness upon production (i.e., the coatings produced are too stiff and have low tensile strength).

More recently, and to overcome at least the stiffness problem, homopolymer networks containing cyanoacrylate-functionalized multi-arm polyisobutylene stars have been employed to provide more flexibility and rubberyness. These homopolymer networks have been developed and patented. The production of such polyisobutylenes provide for a core (Ø) with a desired number of polyisobutylene arms extending therefrom.

There are many potential biomedical applications with polyisobutylene with attachment of various polymers at the end of each arm. One clinical example where polyisobutylene has been adopted is poly(styrene-b-isobutylene-b-styrene), which is currently used as a coating in the Taxus® Drug Eluting Stent. Another potential application is for all applications where 2-octyl cyanoacrylate (Dermabond®) is currently employed and more flexibility is required.

To that end, cyanoacrylate-telechelic three-arm star polyisobutylenes have been prepared. Cyanoacrylate-telechelic three-arm star polyisobutylenes, Ø(PIB-CA)$_3$, were first prepared in 1991. A low viscosity syringible and injectable homopolymer functionalized with ethyl cyanoacrylate (i.e., Et-CA) was subsequently developed in 2007. It was found that a bolus of covalently linked PIB rubber "superglue" was created when Ø(PIB-CA)$_3$ was injected into (egg) protein and the properties could be controlled by addition of poly-ethyl-2-cyanoacrylate. On its own, Ø(PIB-CA)$_3$ homonetwork has a tensile strength of 1.6 MPa, Young's Modulus of 4.9 MPa, and an elongation of 70%. Comparatively, the tensile strength of clinically available 2-octyl cyanoacrylate based "superglue", Dermabond® (Ethicon, J&J) and SurgiSeal™ (Adhezion Biomedical), is less than 0.1 MPa.

Furthermore, it was found that cyanoacrylate-ended tritelechelic polyisobutylene Ø(PIB-CA)$_3$ (Mn~2500 g/mol or more) are nontoxic in rats in vivo. Without being bound by theory, it is believed that the biocompatible high barrier rubbery PIB moiety effectively envelops and shields the noxious cyanoacrylate groups from the surrounding tissue and the permanently sequestered -CA groups are rendered harmless. However, too high molecular weight Ø(PIB-CA)$_3$ could also render the benefit of the -CA groups useless as well, as the rate of polymerization would be greatly slowed.

As noted above, it took several years for the production of a co-network of Ø(PIB-CA)$_3$ and Et-CA. This is because Et-CA is not miscible with Ø(PIB-CA)$_3$. It was only by way of mechanical means (i.e., a dual injectable syringe) that the two components could be brought into contact with each other at a particular site for use. Moreover, the amount and molecular weight of Et-CA was such that only small units of 1 to 6 Et-CA units could be used. Accordingly, the result was the production of the mixture of a homonetwork of Ø(PIB-CA)$_3$ and Et-CA homopolymer. That is, the molar ratio of the Ø(PIB-CA)$_3$ to Et-CA was so high that the resultant product is today considered a network, wherein the Et-CA could be thought of as a crosslinker, rather than a polymer portion of a co-network of Ø(PIB-CA)$_3$ and Et-CA. Thus, other alternative networks to Ø(PIB-CA)$_3$ and Et-CA were sought.

Even more recently, new co-networks consisting of relatively low molecular weight Ø(PIB-CA)$_3$ (Mn=1,000-4,000 g/mole) and 2-octyl cyanoacrylate (Oct-CA) have been developed. These low molecular weight Ø(PIB-CA)$_3$ and Oct-CA are miscible liquids and when reacted with a weak nucleophile (as an initiator) will form a co-network. It has been found, however, that these polymer co-networks lack the mechanical properties desirable in a number of biomedical applications. Polymer co-networks formed from higher molecular weight Ø(PIB-CA)$_3$ (Mn>6,000 g/mole) and Oct-CA, on the other hand, have been found to have excellent mechanical properties but, because High-Ø(PIB-CA)$_3$ and Oct-CA, are not fully miscible, a solvent for both High-Ø (PIB-CA)$_3$ and Oct-CA, such as tetrahydrofuran (THF), must be used to permit miscibility. These solvents, however, are generally toxic and cannot be used in many medical and biological applications.

Accordingly, the need exists in the art for other co-networks formed by polymerizing tri-telechelic cyanoacrylate-functionalized polyisobutylene (Ø(PIB-CA)$_3$) and 2-octyl cyanoacrylate (Oct-CA) that have the desired mechanical characteristics, yet do not contain, or otherwise require for use, toxic solvents.

SUMMARY OF THE INVENTION

In general outline, the present invention is directed to a substantially homogeneous miscible liquid adhesive composition comprising: a relatively high number average molecular weight (i.e., having an Mn equal to greater than 5,001-10,000 g/mol and preferably greater than 6,000 g/mol) 3- or 4-arm star polymer having polyisobutylene chains terminated with cyanoacrylate groups (High-Ø(PIB-CA)$_3$); 2-octyl cyanoacrylate (Oct-CA); and a relatively low molecular weight (i.e., having an Mn equal to or less than 1,000-4,999 g/mol, and preferably less than 4,000 g/mol) 3- or 4-arm star polymer having polyisobutylene chains terminated with cyanoacrylate groups (Low-Ø(PIB-CA)$_3$), which does not contain a solvent and when reacted with a nucleophile, such as water or an initiator, forms a co-network suitable for any of a number of biomedical applications, from wound closure and healing of skin tissue, to sealant for surgical cuts. As will be discussed in more detail below, the Low-Ø(PIB-CA)$_3$ compatibilizes the High-Ø(PIB-CA)$_3$ and Oct-CA but appears to have little or no impact on the mechanical properties of the co-network.

In a first aspect, the present invention is directed to a homogeneous miscible liquid adhesive composition useful for wound closure and skin protection comprising: a first 3- or 4-arm star polymer comprising polyisobutylene terminated with cyanoacrylate groups and having a high number average molecular weight of from about 6,000 g/mole to about 10,000 g/mole; 2-octyl cyanoacrylate; and a second 3- or 4-arm star polymer comprising polyisobutylene terminated with cyanoacrylate groups and having a low number average molecular weight of from about 1,000 g/mole to about 4,000 g/mole. In some embodiments, the homogeneous miscible liquid adhesive composition does not contain a solvent.

In one or more embodiments, the homogeneous miscible liquid adhesive composition of the present invention includes any one or more of the above referenced embodiments of the first aspect of the present invention wherein said first cyanoacrylate tri-telechelic star polymer has a number average molecular weight of about 6,500 g/mole. In one or more embodiments, the homogeneous miscible liquid adhesive composition of the present invention includes any one or more of the above referenced embodiments of the first aspect of the present invention wherein said second cyanoacrylate tri-telechelic star polymer has a number average molecular weight of about 3,000 g/mole.

In one or more embodiments, the homogeneous miscible liquid adhesive composition of the present invention includes any one or more of the above referenced embodiments of the first aspect of the present invention wherein said first cyanoacrylate tri-telechelic star polymer comprises from about 0.1% by weight to about 10% by weight of said homogeneous liquid adhesive composition; said 2-octyl cyanoacrylate comprises from about 50% by weight to about 75% by weight of said homogeneous liquid adhesive composition; and said second cyanoacrylate tri-telechelic star polymer comprises from about 20% by weight to about 40% by weight of said homogeneous liquid adhesive composition. In one or more embodiments, the homogeneous miscible liquid adhesive composition of the present invention includes any one or more of the above referenced embodiments of the first aspect of the present invention wherein the ratio of said first cyanoacrylate tri-telechelic star polymer to said second cyanoacrylate tri-telechelic star polymer is at least about 1:3 by weight.

In a second aspect, the present invention is directed to a homogeneous polymer co-network useful for wound closure and skin protection comprising: the residue of a first 3- or 4-arm star polymer, wherein said first 3- or 4-arm star polymer comprises polyisobutylene terminated with cyanoacrylate groups and has a number average molecular weight of from about 6,000 g/mole to about 10,000 g/mole; the residue of 2-octyl cyanoacrylate; and the residue of a second 3- or 4-arm star polymer, wherein said second 3- or 4-arm star polymer comprises polyisobutylene terminated with cyanoacrylate groups and has a number average molecular weight of from about 1,000 g/mole to about 4,000 g/mole. In some of these embodiments, the cyanoacrylate tri-telechelic star polymer has a number average molecular weight of about 6,500 g/mole. In one or more embodiments, the homogeneous polymer co-network of the present invention includes any one or more of the above referenced embodiments of the second aspect of the present invention wherein said second cyanoacrylate tri-telechelic star polymer has a number average molecular weight of about 3,000 g/mole.

In one or more embodiments, the homogeneous polymer co-network of the present invention includes any one or more of the above referenced embodiments of the second aspect of the present invention having a tensile strength of from about 3 MPa to about 6 MPa. In one or more embodiments, the homogeneous polymer co-network of the present invention includes any one or more of the above referenced embodiments of the second aspect of the present invention having a tensile elongation of from about 60% to about 70%. In one or more embodiments, the homogeneous polymer co-network of the present invention includes any one or more of the above referenced embodiments of the second aspect of the present invention wherein said first cyanoacrylate tri-telechelic star polymer comprises from about 0.1% by weight to about 10% by weight of said liquid adhesive composition; said 2-octyl cyanoacrylate comprises from about 50% by weight to about 75% by weight of said liquid adhesive composition; and said second cyanoacrylate tritelechelic star polymer comprises from about 20% by weight to about 40% by weight of said homogeneous polymer co-network. In one or more embodiments, the homogeneous polymer co-network of the present invention includes any one or more of the above referenced embodiments of the second aspect of the present invention wherein the ratio of the residue of said first cyanoacrylate tri-telechelic star polymer to the residue of said second cyanoacrylate tri-telechelic star polymer is at least about 1:3.

In a third aspect, the present invention is directed to a homogeneous polymer co-network useful for wound closure and skin protection comprising the reaction product of: a first 3-arm star polymer comprising polyisobutylene terminated with cyanoacrylate groups and having a high number average molecular weight of from about 6,000 g/mole to about 10,000 g/mole; 2-octo cyanoacrylate; a second 3-arm star polymer comprising polyisobutylene terminated with cyanoacrylate groups and having a low number average molecular weight of from about 1,000 g/mole to about 4,000 g/mole; and a nucleophile, such as water or a suitable initiator. In some embodiments, the first cyanoacrylate tri-telechelic star polymer has a number average molecular weight of about 6,500 g/mole.

In one or more embodiments, the homogeneous polymer co-network of the present invention includes any one or more of the above referenced embodiments of the third aspect of the present invention wherein said second cyanoacrylate tri-telechelic star polymer has a number average molecular weight of about 3,000 g/mole. In one or more embodiments, the homogeneous polymer co-network of the present invention includes any one or more of the above referenced embodiments of the third aspect of the present invention having a tensile strength of from about 3 MPa to about 6 MPa. In one or more embodiments, the homogeneous polymer co-network of the present invention includes any one or more of the above referenced embodiments of the third aspect of the present invention having a tensile elongation of from about 60% to about 70%.

In one or more embodiments, the homogeneous polymer co-network of the present invention includes any one or more of the above referenced embodiments of the third aspect of the present invention wherein said first cyanoacrylate tri-telechelic star polymer comprises from about 0.1% by weight to about 10% by weight of said homogeneous polymer co-network; said 2-octyl cyanoacrylate comprises from about 50% by weight to about 75% by weight of said homogeneous polymer co-network; and said second cyanoacrylate tri-telechelic star polymer comprises from about 20% by weight to about 40% by weight of said homogeneous polymer co-network. In one or more embodiments, the homogeneous polymer co-network of the present invention includes any one or more of the above referenced embodiments of the third aspect of the present invention wherein the ratio of the said first cyanoacrylate tri-telechelic star polymer to of said second cyanoacrylate tri-telechelic star polymer is from about 1:3 to about 1:6 by weight.

In a fourth aspect, the present invention is directed to a method for forming a homogeneous polymer co-network useful for wound closure and skin protection comprising: preparing a homogeneous liquid adhesive composition having a first 3-arm star polymer comprising polyisobutylene terminated with cyanoacrylate groups and having a number average molecular weight of from about 6,000 g/mole to about 10,000 g/mole; 2-octyl cyanoacrylate; and a second 3-arm star polymer comprising polyisobutylene terminated with cyanoacrylate groups and having a number average molecular weight of from about 1,000 g/mole to about 4,000 g/mole; And then applying said homogeneous liquid adhesive composition to a tissue having one or more available nucleophiles, wherein said nucleophiles cause said homogeneous liquid adhesive composition to co-polymerize to form a homogeneous polymer co-network comprising the residues of said first cyanoacrylate tri-telechelic star polymer, said second cyanoacrylate tri-telechelic star polymer, and said 2-octyl cyanoacrylate.

In some of these embodiments, the first cyanoacrylate tri-telechelic star polymer comprises from about 0.1% by weight to about 10% by weight of said homogeneous liquid adhesive composition; said 2-octyl cyanoacrylate comprises from about 50% by weight to about 75% by weight of said homogeneous liquid adhesive composition; and said second cyanoacrylate tri-telechelic star polymer comprises from about 20% by weight to about 40% by weight of said homogeneous liquid adhesive composition. In one or more embodiments, the method of the present invention includes any one or more of the above referenced embodiments of the fourth aspect of the present invention wherein the ratio of said first cyanoacrylate tri-telechelic star polymer to said second cyanoacrylate tri-telechelic star polymer in said homogeneous liquid adhesive composition is from about 1:3 to about 1:6 by weight.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

In general outline, the present invention is directed to a substantially homogeneous miscible liquid adhesive composition comprising a relatively high number average molecular weight ($M_n$=6,000-10,000 g/mole) 3-arm star polymer having polyisobutylene chains terminated with cyanoacrylate groups (High-$\varnothing(PIB-CA)_3$); 2-octyl cyanoacrylate (Oct-CA); and a relatively low molecular weight ($M_n$=1,000-4,000 g/mole) 3-arm star polymer having polyisobutylene chains terminated with cyanoacrylate groups (Low-Ø(PIB-CA)$_3$), which does not contain a solvent and when reacted with a nucleophile, such as water or an initiator, forms a co-network suitable for any of a number of biomedical applications, from wound closure and healing of skin tissue, to sealant for surgical cuts. As will be discussed in more detail below, the Low-Ø(PIB-CA)$_3$ compatibilizes the High-Ø(PIB-CA)$_3$ and Oct-CA.

In a first aspect, the present invention is directed to a substantially homogeneous miscible liquid adhesive composition useful for wound closure and skin protection comprising: a first 3-arm star polymer comprising polyisobutylene terminated with cyanoacrylate groups and having a high number average molecular weight of from about 6,000 g/mole to about 10,000 g/mole; 2-octyl cyanoacrylate; and a second 3-arm star polymer comprising polyisobutylene terminated with cyanoacrylate groups and having a low number average molecular weight of from about 1,000 g/mole to about 4,000 g/mole, wherein the homogeneous miscible liquid adhesive composition does not contain a solvent. To begin, it will be appreciated that the chemical formulas of the starting materials are shown below as formulas (I) and (II), below.

It will be understood by those in the art that both High-Ø (PIB-CA)$_3$ and Low-Ø(PIB-CA)$_3$ molecules will have the general structure shown in Formula II, differing only in the length of the polyisobutylene (PIB) chains connecting the cyanoacrylate (CA) groups to the star polymer core.

Figure 1A:
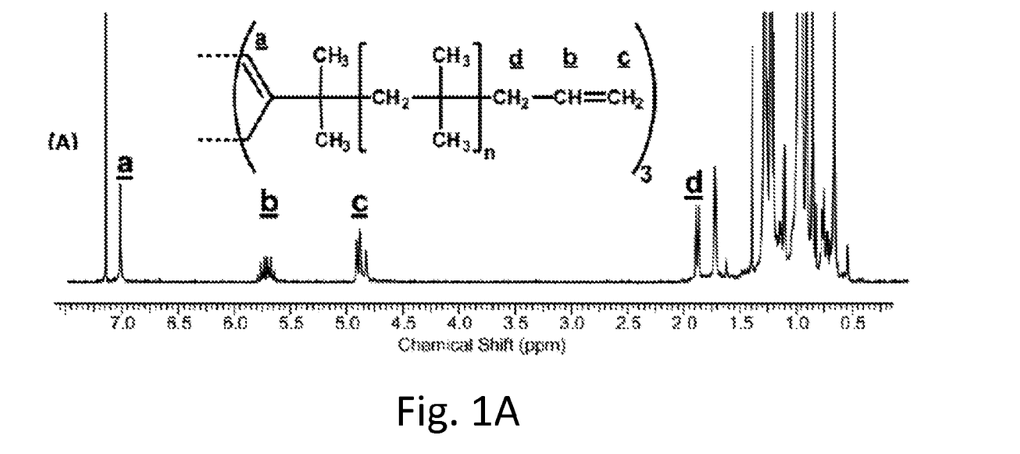
FIG. 1A is the H NMR spectrum of an allyl-terminated three-arm star PIB intermediate.
Figure 1B:
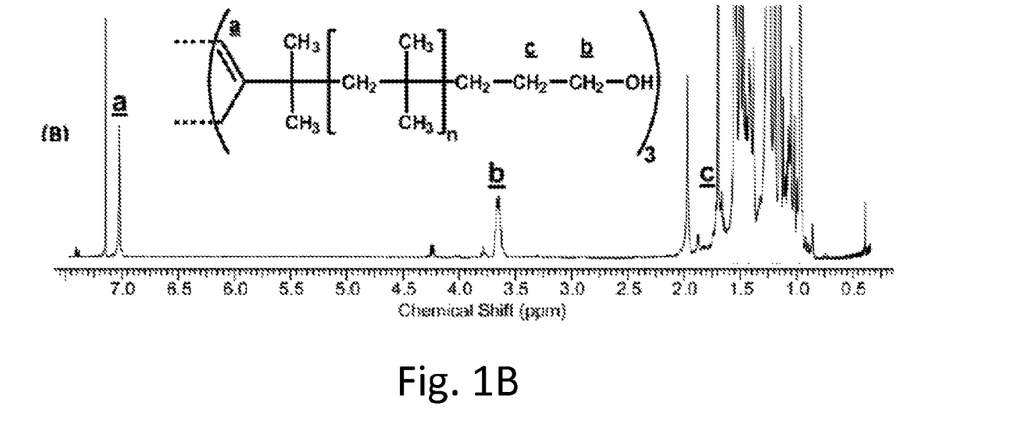
FIG. 1B is the H NMR spectrum of a hydroxyl-terminated three arm star PIB intermediate.
Figure 1C:
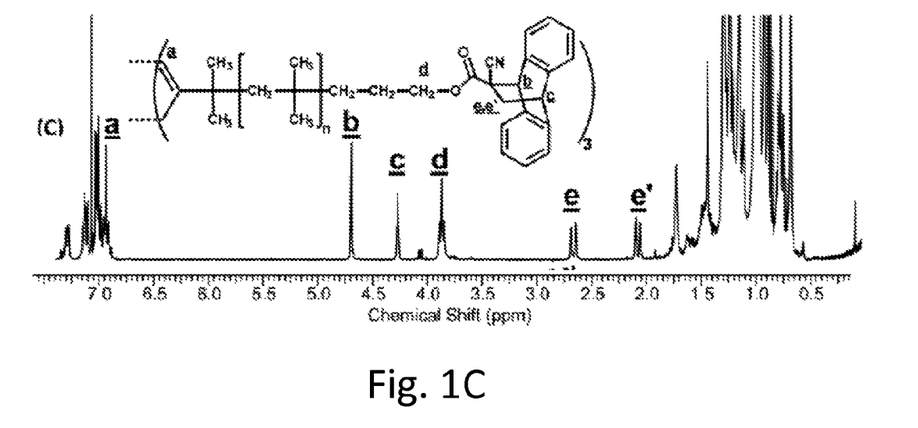
FIG. 1C is the H NMR spectrum of an anthracene/cyanoacrylate adduct three arm star PIB intermediate.
Figure 1D:
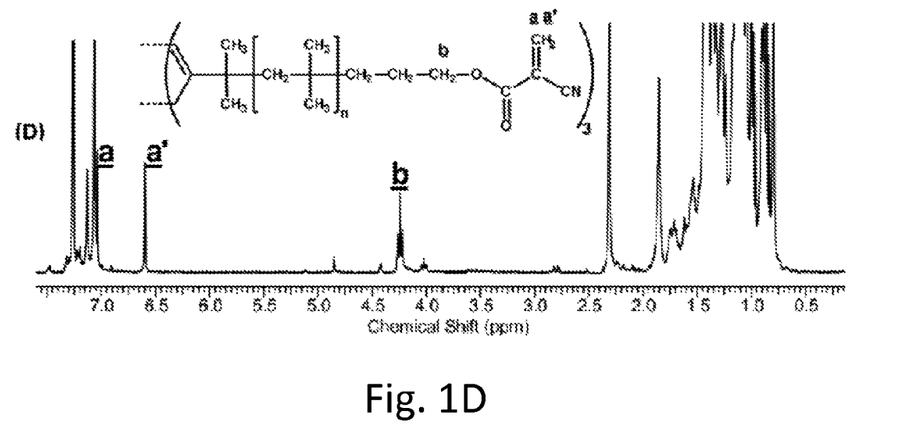
FIG. 1D is the H NMR spectrum the cyanoacrylate-tri-telechelic PIB, $\varnothing(PIB-CA)_3$ final product.
Figure 2:
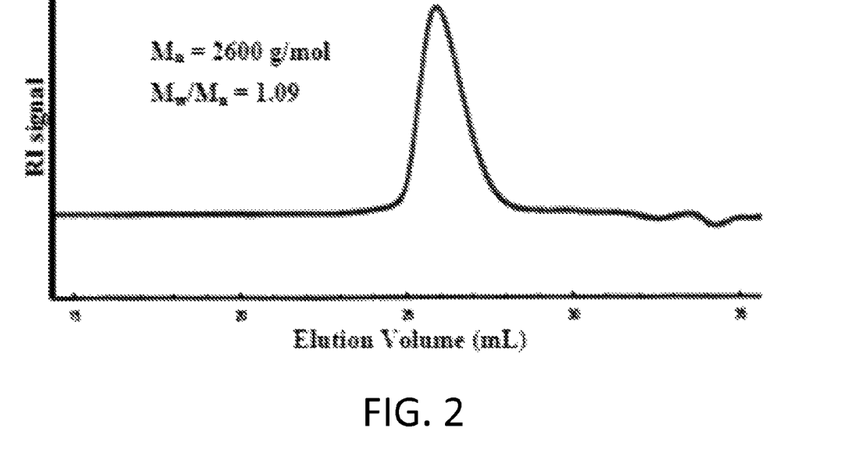
FIG. 2 is the GPC trace of a representative three-arm star allyl-tri-telechelic polyisobutylene.

The preparation of Ø(PIB-CA)$_3$ is well known and has been described in at least US Patent Application Publication No. US2014/0073743 A1, the disclosure of which is hereby incorporated by reference. Briefly, the synthesis involves the living polymerization of isobutylene induced by a trifunctional initiator and termination with allyltrimethylsilane. The 3-arm star allyl-terminated intermediate so obtained is converted quantitatively to the hydroxyl or bromine terminated intermediate, which is then reacted with anthracene-protected cyanoacryloyl chloride, or, preferentially, with 2-cyanoacrylic acid. Finally, the protective anthracene group was removed by treatment with maleic anhydride in refluxing xylene for about 10 hours to yield the target Ø(PIB-CA)$_3$. FIGS. 1A-C show the NMR spectra of the intermediates (allyl-, hydroxyl-, and anthracene/cyanoacrylate adduct) and FIG. 1D shows the NMR spectra of the final product (cyanoacrylate-tri-telechelic PIBs, Ø(PIB-CA)$_3$). FIG. 2 displays the GPC trace of the first intermediate (allyl-), indicating the presence of a homogenous well-defined material with narrow molecular weight dispersity. The GPC traces of the other intermediates were similarly narrow.

Earlier syntheses of Ø(PIB-CA)$_3$ carried out by the use of (protected) cyanoacryloyl chloride consistently gave yellow products. Efforts to remove the color (repeated precipitations, column chromatography, treatment with activated carbon) were only partially successful. The source of the discoloration is unknown (most likely due to traces of impurities associated with the use of thionyl chloride). In contrast, esterification of a tri-telechelic star polymer comprising polyisobutylene terminated with hydroxyl groups (Ø(PIB-OH)$_3$) (See Formula IV, Scheme 1 below) with anthracene-protected 2-cyanoacrylic acid (See Formula III, below) gave colorless products (See Formula V, below). The following equation outlines this preferred method for the synthesis of Ø(PIB-CA)$_3$ (See Formula II, above) (The protective anthracene group, indicated by A in the semicircle, can be readily removed by maleic anhydride):

Thus, in a 50 mL Schlenk flask with a magnetic stir bar were placed under a blanket of nitrogen Ø(PIB-OH)$_3$ (1.227 g, $M_n$=2500 g/mol) (Formula IV), anthracene-protected 2-cyano carboxylic acid adduct (1.333 g) (Formula III), and 4-dimethylamino pyridine (DMAP, 71.3 mg) dissolved in dichloromethane (DCM, 25 mL). Then the solution was cooled to 0° C., N,N'-dicyclohexylcarbodiimide (DCC, 1.0648 g) was added, the solution was stirred for 30 min at 0° C., and then overnight at room temperature. The precipitated urea was filtered off, the DCM was evaporated in vacuo, and the viscous residue was dissolved in THF and purified by two precipitations into methanol to produce an anthracene/cyanoacrylate adduct three arm star PIB intermediate (Formula V). Finally, to yield Ø(PIB-CA)$_3$ (Formula II, above), the protective anthracene group was removed by treatment with maleic anhydride in refluxing xylene for 8 hrs. According to NMR analysis the yields of protection and deprotection were typically ~60 and ~90%, respectively. Similar yields have been obtained by others who used the same protection/deprotection technique.

The preparation of Oct-CA is likewise well known in the art and will not be described herein in detail. Oct-CA is commercially available from a variety of sources, including, but not limited to, Chenso Inc. (Champions Gate, Fla.).

And while Ø(PIB-CA)$_3$ polymers having a wide range of number average molecular weights ($M_n$) are known in the art, the present application relates to Ø(PIB-CA)$_3$ polymers having number average molecular weights ($M_n$) of from about 1,000 g/mole to about 10,000 g/mole. As used herein, the terms "low" or "relatively low" as applied to the molecular weight of Ø(PIB-CA)$_3$ polymers refers to cyanoacrylate tri-telechelic star polymers having the general structure shown in Formula II that are miscible with 2-octyl cyanoacrylate (Oct-CA) and have a $M_n$ of from about 1,000 g/mole to about 4,000 g/mole. (Low-Ø(PIB-CA)$_3$). The fact that Low-Ø(PIB-CA)$_3$, and Oct-CA are miscible was surprising because the very similar cyanoacrylates (methyl-, ethyl-, and butyl-CA) are completely immiscible with (Ø(PIB-CA)$_3$).

Similarly, while much larger Ø(PIB-CA)$_3$ polymers may be known in the art, as used herein, the terms "high" or "relatively high" as applied to Ø(PIB-CA)$_3$ polymers refers to 3-arm star polymers having polyisobutylene chains terminated with cyanoacrylate groups (High-Ø(PIB-CA)$_3$) and the general structure shown in Formula II, that have a $M_n$ of from about 6,000 g/mole to about 10,000 g/mole. These polymers are not fully miscible with Oct-CA.

As set forth above, in various embodiments, the present invention is directed to a substantially homogeneous miscible liquid adhesive composition useful for wound closure and skin protection. This liquid adhesive composition comprises High-Ø(PIB-CA)$_3$ and Oct-CA, which are both liquids at room temperature, and as set forth above, not fully miscible. Accordingly, Low-Ø(PIB-CA)$_3$, which is also a liquid at room temperature and is known to be miscible with both High-Ø(PIB-CA)$_3$ and Oct-CA, is added as a compatibilizing agent. The addition of the Low-Ø(PIB-CA)$_3$ renders the High-Ø(PIB-CA)$_3$ and Oct-CA fully miscible with each other, thereby generating a substantially homogeneous miscible liquid adhesive composition. Importantly, no solvents are necessary to create this liquid adhesive composition.

In some embodiments, the High-Ø(PIB-CA)$_3$ in the liquid adhesive composition may have a $M_n$ of from about 6,000 g/mole to about 10,000 g/mole. In some other embodiments, the High-Ø(PIB-CA)$_3$ in the liquid adhesive composition may have a $M_n$ of from about 6,000 g/mole to about 9,000 g/mole. In some other embodiments, the High-Ø(PIB-CA)$_3$ in the liquid adhesive composition may have a $M_n$ of from about 6,000 g/mole to about 8,000 g/mole. In some other embodiments, the High-Ø(PIB-CA)$_3$ in the liquid adhesive composition may have a $M_n$ of from about 6,000 g/mole to about 7,000 g/mole. In some other embodiments, the High-Ø(PIB-CA)$_3$ in the liquid adhesive composition may have a $M_n$ of from about 6,000 g/mole to about 6,500 g/mole. In some other embodiments, the High-Ø(PIB-CA)$_3$ in the liquid adhesive composition may have a $M_n$ of from about 6,500 g/mole to about 9,000 g/mole. In some other embodiments, the High-Ø(PIB-CA)$_3$ in the liquid adhesive composition may have a $M_n$ of from about 6,500 g/mole to about 8,000 g/mole. In some other embodiments, the High-Ø(PIB-CA)$_3$ in the liquid adhesive composition may have a $M_n$ of about 6,500 g/mole.

In some embodiments, the Low-Ø(PIB-CA)$_3$ in the liquid adhesive composition may have a $M_n$ of from about 1,000 g/mole to about 4,000 g/mole. In some other embodiments, the Low-Ø(PIB-CA)$_3$ in the liquid adhesive composition may have a $M_n$ of from about 1,000 g/mole to about 3,500 g/mole. In some other embodiments, the Low-Ø(PIB-CA)$_3$ in the liquid adhesive composition may have a $M_n$ of from about 1,000 g/mole to about 3,000 g/mole. In some other embodiments, the Low-Ø(PIB-CA)$_3$ in the liquid adhesive composition may have a $M_n$ of from about 1,000 g/mole to about 2,500 g/mole. In some other embodiments, the Low-Ø(PIB-CA)$_3$ in the liquid adhesive composition may have a $M_n$ of from about 2,000 g/mole to about 4,000 g/mole. In some other embodiments, the Low-Ø(PIB-CA)$_3$ in the liquid adhesive composition may have a $M_n$ of from about 2,500 g/mole to about 4,000 g/mole. In some other embodiments, the Low-Ø(PIB-CA)$_3$ in the liquid adhesive composition may have a $M_n$ of from about 3,000 g/mole to about 4,000 g/mole. In some other embodiments, the Low-Ø(PIB-CA)$_3$ in the liquid adhesive composition may have a $M_n$ of from about 2,500 g/mole to about 3,500 g/mole. In some other embodiments, the Low-Ø(PIB-CA)$_3$ in the liquid adhesive composition may have a $M_n$ of about 3,000 g/mole.

In some embodiments, the High-Ø(PIB-CA)$_3$ may comprise from about 0.1% by weight to about 10% by weight of the liquid adhesive composition. In some other embodiments, the High-Ø(PIB-CA)$_3$ may comprise from about 0.5% by weight to about 10% by weight of the liquid adhesive composition. In some other embodiments, the High-Ø(PIB-CA)$_3$ may comprise from about 0.1% by weight to about 8% by weight of the liquid adhesive composition. In some other embodiments, the High-Ø(PIB-CA)$_3$ may comprise from about 0.1% by weight to about 5% by weight of the liquid adhesive composition. In some other embodiments, the High-Ø(PIB-CA)$_3$ may comprise from about 3% by weight to about 10% by weight of the liquid adhesive composition. In some other embodiments, the High-Ø(PIB-CA)$_3$ may comprise from about 5% by weight to about 10% by weight of the liquid adhesive composition. In some other embodiments, the High-Ø(PIB-CA)$_3$ may comprise from about 8% by weight to about 10% by weight of the liquid adhesive composition. In some other embodiments, the High-Ø(PIB-CA)$_3$ may comprise from about 3% by weight to about 10% by weight of the liquid adhesive composition. In some other embodiments, the High-Ø(PIB-CA)$_3$ may comprise about 5% by weight of the liquid adhesive composition.

In some embodiments, the 2-octyl cyanoacrylate (Oct-CA) may comprise from about 50% by weight to about 75% by weight of the liquid adhesive composition. In some other embodiments, the Oct-CA may comprise from about 50% by weight to about 70% by weight of the liquid adhesive composition. In some other embodiments, the Oct-CA may comprise from about 50% by weight to about 65% by weight of the liquid adhesive composition. In some other embodiments, the Oct-CA may comprise from about 50% by weight to about 60% by weight of the liquid adhesive composition. In some other embodiments, the Oct-CA may comprise from about 55% by weight to about 70% by weight of the liquid adhesive composition. In some other embodiments, the Oct-CA may comprise from about 60% by weight to about 75% by weight of the liquid adhesive composition. In some other embodiments, the Oct-CA may comprise from about 65% by weight to about 75% by weight of the liquid adhesive composition. In some other embodiments, the Oct-CA may comprise about 74% by weight of the liquid adhesive composition.

In some embodiments, the Low-Ø(PIB-CA)$_3$ may comprise from about 20% by weight to about 40% by weight of the liquid adhesive composition. In some other embodiments, the Low-Ø(PIB-CA)$_3$ may comprise from about 20% by weight to about 35% by weight of the liquid adhesive composition. In some other embodiments, the Low-Ø(PIB-CA)$_3$ may comprise from about 20% by weight to about 30% by weight of the liquid adhesive composition. In some other embodiments, the Low-Ø(PIB-CA)$_3$ may comprise from about 20% by weight to about 25% by weight of the liquid adhesive composition. In some other embodiments, the Low-Ø(PIB-CA)$_3$ may comprise from about 25% by weight to about 40% by weight of the liquid adhesive composition. In some other embodiments, the Low-Ø(PIB-CA)$_3$ may comprise from about 30% by weight to about 40% by weight of the liquid adhesive composition. In some other embodiments, the Low-Ø(PIB-CA)$_3$ may comprise about 21% by weight of the liquid adhesive composition.

In one embodiment, the liquid adhesive composition may comprise 5% by weight of High-Ø(PIB-CA)$_3$, 21% by weight of Low-Ø(PIB-CA)$_3$, and 74% by weight of Oct-CA.

In some embodiments, the weight ratio of High-Ø(PIB-CA)$_3$ to Low-Ø(PIB-CA)$_3$ in the liquid adhesive composition may be from about 1:3 to about 1:6. In some other embodiments, the weight ratio of High-Ø(PIB-CA)$_3$ to Low-Ø(PIB-CA)$_3$ in the liquid adhesive composition may be from about 1:4 to about 1:5. In some other embodiments, the weight ratio of High-Ø(PIB-CA)$_3$ to Low-Ø(PIB-CA)$_3$ in the liquid adhesive composition may be from about 1:3 to about 1:5. In some other embodiments, the weight ratio of High-Ø(PIB-CA)$_3$ to Low-Ø(PIB-CA)$_3$ in the liquid adhesive composition may be from about 1:3 to about 1:4. In some other embodiments, the weight ratio of High-Ø(PIB-CA)$_3$ to Low-Ø(PIB-CA)$_3$ in the liquid adhesive composition may be from about 1:4 to about 1:6. In some other embodiments, the weight ratio of High-Ø(PIB-CA)$_3$ to Low-Ø(PIB-CA)$_3$ in the liquid adhesive composition may be from about 1:5 to about 1:6. In some other embodiments, the weight ratio of High-Ø(PIB-CA)$_3$ to Low-Ø(PIB-CA)$_3$ in the liquid adhesive composition polymer is at least about 1:3.

In other aspects, the present invention is directed to the substantially homogeneous polymer co-networks formed as the reaction product of the substantially homogeneous miscible liquid adhesive compositions described above and a nucleophile, such as water or a suitable initiator. As will be appreciated by those of ordinary skill in the art, the High-Ø(PIB-CA)$_3$, Low-Ø(PIB-CA)$_3$ and Oct-CA molecules in the liquid adhesive compositions described above will begin to co-polymerize in the presence of even a weak nucleophile, such as water, to form a co-network comprising the residues of the High-Ø(PIB-CA)$_3$, Low-Ø(PIB-CA)$_3$ and Oct-CA molecules that made up the liquid adhesive composition. As used herein, the term "residue(s)" is used to refer generally to the part of a monomer or other chemical unit that has been incorporated into a polymer or large molecule. Here, by extension, the residues of the High-Ø(PIB-CA)$_3$, Low-Ø(PIB-CA)$_3$ and Oct-CA molecules are the portions of the these molecules that are incorporated into homogeneous polymer co-networks of the present invention.

Because High-Ø(PIB-CA)$_3$, Low-Ø(PIB-CA)$_3$ and Oct-CA all contain polymerizable cyanoacrylate (CA) groups they can readily produce polymer co-networks. And since the inherent reactivity of the CA functional group is independent of the molecular weight of the polymer it is attached to, it may be safely assumed that the reactivities of the CA groups of Oct-CA and High and Low-Ø(PIB-CA)$_3$ molecules are essentially identical (i.e., their reactivity ratios are unity). The composition of the co-network will, therefore, reflect the relative composition of the starting monomers and the co-network composition can therefore, be controlled by controlling the relative amounts of High-Ø(PIB-CA)$_3$, Low-Ø(PIB-CA)$_3$ and Oct-CA.

Accordingly, the substantially homogeneous polymer co-networks of the present invention may have any composition that reflects the composition of any of the liquid polymer adhesives described above. In some embodiments, the substantially homogeneous polymer co-networks of the present invention may comprise from about 0.1% by weight to about 10% by weight of High-Ø(PIB-CA)$_3$, said from about 50% by weight to about 75% by weight of Oct-CA, and from about 20% by weight to about 40% by weight of Low-Ø(PIB-CA)$_3$. In one embodiment the substantially homogeneous polymer co-networks of the present invention may comprise 5% by weight of High-Ø(PIB-CA)$_3$, 21% by weight of Low-Ø(PIB-CA)$_3$, and 74% by weight of Oct-CA.

Further, the substantially homogeneous polymer co-networks of the present invention are flexible and have been shown to have excellent mechanical properties. In some embodiments, these co-networks have been shown to have a tensile strength of from about 3 MPa to about 6 MPa. In some of these embodiments, the co-networks have been shown to have a tensile strength of from about 4 MPa to about 5 MPa. In some other of these embodiments, the co-networks have been shown to have a tensile strength of from about 5 MPa to about 6 MPa. In some other of these embodiments, the co-networks have been shown to have a tensile strength of about 4.1. Similarly, in some embodiments, these co-networks have been shown to have a tensile elongation of from about 60% to about 70%. In some of these embodiments, the co-networks have been shown to have a tensile elongation of from about 60% to about 68%. In some of these embodiments, the co-networks have been shown to have a tensile elongation of from about 60% to about 65%. In some of these embodiments, the co-networks have been shown to have a tensile elongation of from about 65% to about 68%. In some of these embodiments, the co-networks have been shown to have a tensile elongation of from about 65% to about 70%. In some of these embodiments, the co-networks have been shown to have a tensile elongation of from about 63% to about 68%. In some of these embodiments, the co-networks have been shown to have a tensile elongation of about 65%.

Figure 3:
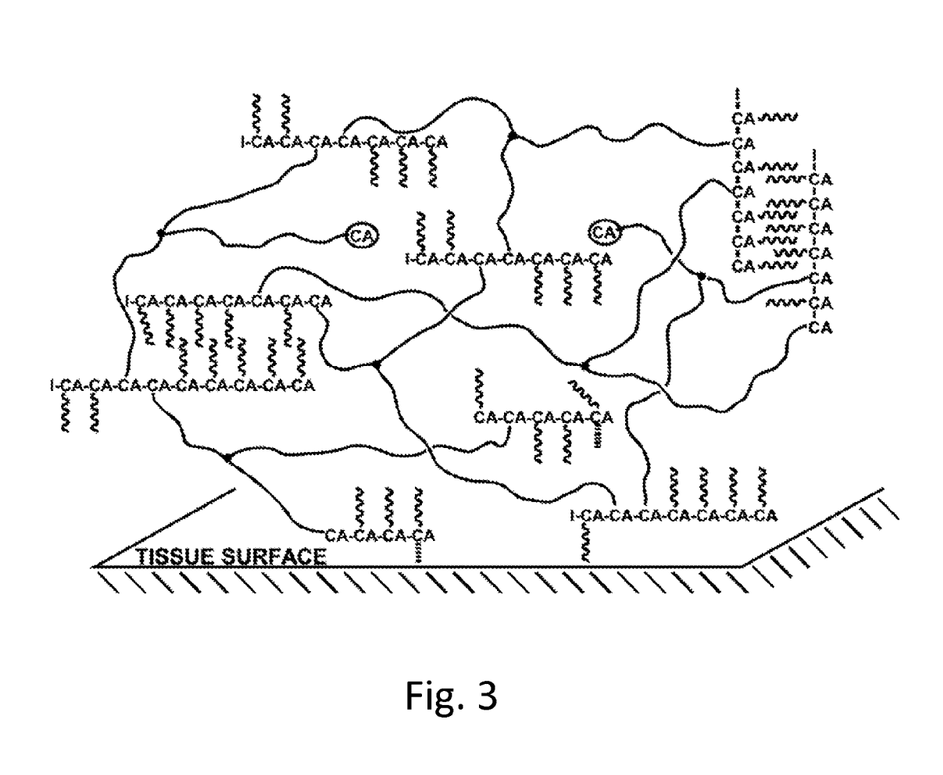
FIG. 3 is an idealized microstructure representation of a polyisobutylene co-network that arises from a homogeneous 50/50 wt/wt polymer blend of Oct-CA plus $\varnothing(PIB-CA)_3$ upon the addition of an initiator at room temperature, [wherein the poly(Oct-CA) sequences polymerized are of sufficient length (i.e., greater than 3 CA units) to form separate coalesced phases whose $T_g$ can be identified by appropriate instrumentation, such as Differential Scanning calorimetry (DSC) or Dynamic Mechanical Thermal Analysis (DMTA)

With more particular respect to the present invention, FIG. 3 shows an idealized microstructure of a co-network that arises from a homogeneous 50/50 wt/wt blend of Oct-CA and Ø(PIB-CA)$_3$ upon the addition of an initiator at room temperature. In these co-networks, the poly(Oct-CA) sequences are of sufficient length (i.e., greater than 3 CA units) to form separate coalesced phases whose $T_g$ can be identified by appropriate instrumentation. As shown in FIG. 3, the 50/50 wt/wt Poly[Oct-CA-co-Ø(PIB-CA)$_3$] co-network is represented, with the wiggly lines being PIB, I being the initiator, CA--- being the Oct-CA bonded to or available for bonding to the skin surface. The CA of multiple units being the Poly(Oct-CA), the CAs in the circle being "useless" CA groups entrapped in matrix, and the • being the aromatic center of Ø(PIB-CA)$_3$. Again the presence of catenated/entrapped crosslinks and PIB loops should be noted. Importantly, the polymerization of CA groups is initiated by a purposely added initiator (I), in addition to a nucleophilic group (N or O) in the epidermis (---), or by traces of moisture (not shown). It should be appreciated, however, that FIG. 3 is intended to show a generalized microstructure for a Oct-CA/Ø(PIB-CA)$_3$ co-network and its interaction with skin, and does not distinguish between High and low-Ø(PIB-CA)$_3$ molecules, which differ only by the length of the PIB chains.

In another aspect, the present invention is directed to methods of making the substantially homogeneous polymer co-networks of the present invention described above. Because it is a liquid, the liquid adhesive compositions of the present invention can be delivered by essentially any means known in the art to form a coating or film that preferably rapidly solidifies into a robust rubbery protecting barrier. In one embodiment, the liquid adhesive composition may be delivered by spraying or application via vial with plastic sponge tip to provide a suitable coating or film of the composition onto the desired tissue. In another embodiment, the liquids may be delivered by syringe, injecting the composition to a suitable site, again using the sponge tip. It should be appreciated that, in these embodiments, this sponge performs two critical functions: (a) it helps delivering the active ingredient evenly over the targeted surface, and, more importantly, (b) it contains a key component, the initiator, which induces and accelerates the polymerization of the CA monomer as it is squeezed through the sponge. By allowing such monomer mixtures to polymerize in situ, solid rubbery plugs can form exactly where the mixture was applied, i.e., where the seal is needed.

As set forth above, the copolymerization of Oct-CA with High and Low-Ø(PIB-CA)$_3$ may be initiated by the moisture (i.e., nucleophilic groups such as OH, $NH_2$, etc.) on or within the skin, blood or other living (or dead) tissue itself when one of the liquid adhesive compositions of the present invention described above is sprayed, coated or otherwise applied over wounds or surgical cuts. However, it has been found that the rate of co-polymerization can be significantly increased by the use of a suitable initiator, applied just before application of the liquid adhesive composition to the skin, wound, or surgical cut. The scientific literature mentions a large variety of initiators for the polymerization of alkyl CAs, e.g., water, bases, anions, methanol, amines, phosphines, and alkyl ammonium salts. One of ordinary skill in the art will be able to select a suitable initiator without undue experimentation. Suitable initiators may include, without limitation N,N-dimethyl-p-toluidine (DMT), (commercially available from, at least, Sigma Aldrich Company LLC (St. Louis, Mo.)), azabicyclo[2.2.2]-octane (ABCO), and 1,4-diazabicyclo[2.2.2]-octane (DABCO), (both ABCO and DABCO are commercially available from, at least, Alfa Aesar (Ward Hill, Mass.)).

During the early stages of polymerization the viscosity of the system is relatively low and propagation, i.e., the attack of the first CA anion to Oct-CA and/or Ø(PIB-CA)$_3$ (that yields crosslinking) is relatively unhindered as set forth in the reaction scheme below:

Scheme 2

Formula VI

Formula VII $$R = -\overset{CH_3}{\underset{|}{CH}}-(CH_2)_5CH_3$$

or

—PIB

Formula VIII

Upon further propagation steps, particularly after Ø(PIB-CA)$_3$ incorporation, the viscosity of the system rises very rapidly and the rate of (co)polymerization necessarily drops precipitously. Ultimately, a fraction of CA groups likely become entrapped in the highly viscous matrix and propagation ceases.

Due to the highly hydrophobic matrix, termination, i.e., the permanent annihilation of propagating anions, which likely involves reaction with protons (i.e., moisture), is absent or is very slow in these bulk polymerizations. The mechanical properties of the products may be controlled by controlling the relative proportions of the rubbery PIB and glassy poly(Oct-CA) segments. By increasing the length of the PIB arms, elongations increase and moduli decrease. The longer poly(Oct-CA) sequences would phase separate and may function as reinforcing sites.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is number average molecular weight, temperature is in degrees Centigrade, and pressure is at or near atmospheric.

Materials 2-octyl cyanoacrylate (Oct-CA) was purchased from Chenso Inc. (Champions Gate, Fla.), and they were used without further purification. Tetrahydrofuran, purchased from Aldrich and toluene were thoroughly dried by refluxing and distilling the solvents over sodium and benzophenone. Anthracene-protected 2-cyano carboxylic acid adduct, 4-dimethylamino pyridine (DMAP), and N,N'-dicyclohexylcarbodiimide (DCC) were purchased from Sigma-Aldrich.

Instruments and Procedures

Proton ($^1$H) NMR spectroscopy, (Varian Gemini 300 and 500 MHz instruments and deuterated chloroform as solvent) was used to determine chemical structures, chain-end functionalities and molecular weights ($M_n$).

Gel permeation chromatography (GPC) eluograms were obtained using a Waters GPC instrument equipped with a series of three Waters Styragel-HR columns (HR-1, HR-4E, HR-5E), a refractive index detector (Waters 2414) and a multiangle laser light scattering detector (Dawn EOS, Wyatt Technology). Samples were dissolved in THF, the flow rate was 1 mL THF/min, and column temperature was 35° C.

Stress strain properties of microdumbell-shaped samples were determined with a Texture Analyzer TA.XTplus tester with a 5 kilo load cell at a crosshead speed of 5 mm/min, following ASTM D638-02a. Samples (0.2-0.25 mm thick and 65 mm long) were punched from solution (THF) cast films.

Example 1

Synthesis of Ø(PIB-CA)$_3$

In a 50 mL Schlenk flask with a magnetic stir bar were placed under a blanket of nitrogen Ø(PIB-OH)$_3$ (1.227 g, $M_n$=2500 g/mol), anthracene-protected 2-cyano carboxylic acid adduct (1.333 g), and 4-dimethylamino pyridine (DMAP, 71.3 mg) dissolved in dichloromethane (DCM, 25 mL). Then the solution was cooled to 0° C., N,N'-dicyclohexylcarbodiimide (DCC, 1.0648 g) was added, the solution was stirred for 30 min at 0° C., and then overnight at room temperature. The precipitated urea was filtered off, the DCM was evaporated in vacuo, and the viscous residue was dissolved in THF and purified by two precipitations into methanol. (See Scheme 1 above). Finally, to yield Ø(PIB-CA)$_3$, the protective anthracene group was removed by treatment with maleic anhydride in refluxing xylene for 8 hrs. According to NMR analysis the yields of protection and deprotection were typically ~60 and ~90%, respectively. (See FIGS. 1A-D)

Example 2

Solubility of Oct-CA and Ø(PIB-CA)$_3$

Prior to copolymerizations, the mutual miscibility of Oct-CA and Ø(PIB-CA)$_3$ was investigated. It was found that Oct-CA plus Ø(PIB-CA)$_3$ having a number average molecular weight of 2500 g/mol or more ($M_n$=at least 2500 g/mol) yield optically clear blends in all proportions, indicating that Oct-CA and Ø(PIB-CA)$_3$ are miscible. In contrast, even small amounts (~5%) of Me- and Et-CA are immiscible with Ø(PIB-CA)$_3$ and yield hazy mixtures under the same conditions. Further, it was found that Oct-CA plus Ø(PIB-CA)$_3$ of $M_n$=6,500 g/mol produce in homogeneous mixtures, indicating that the higher molecular weight Ø(PIB-CA)$_3$ is immiscible or only partially miscible with Oct-CA Upon the addition of 10 wt % THF to the hazy Oct-CA/Ø(PIB-CA)$_3$ ($M_n$=6,500 g/mol) mixture, the system became optically clear, indicating miscibility in THF solution.

Example 3

Tensile Strength Testing

Figure 4:
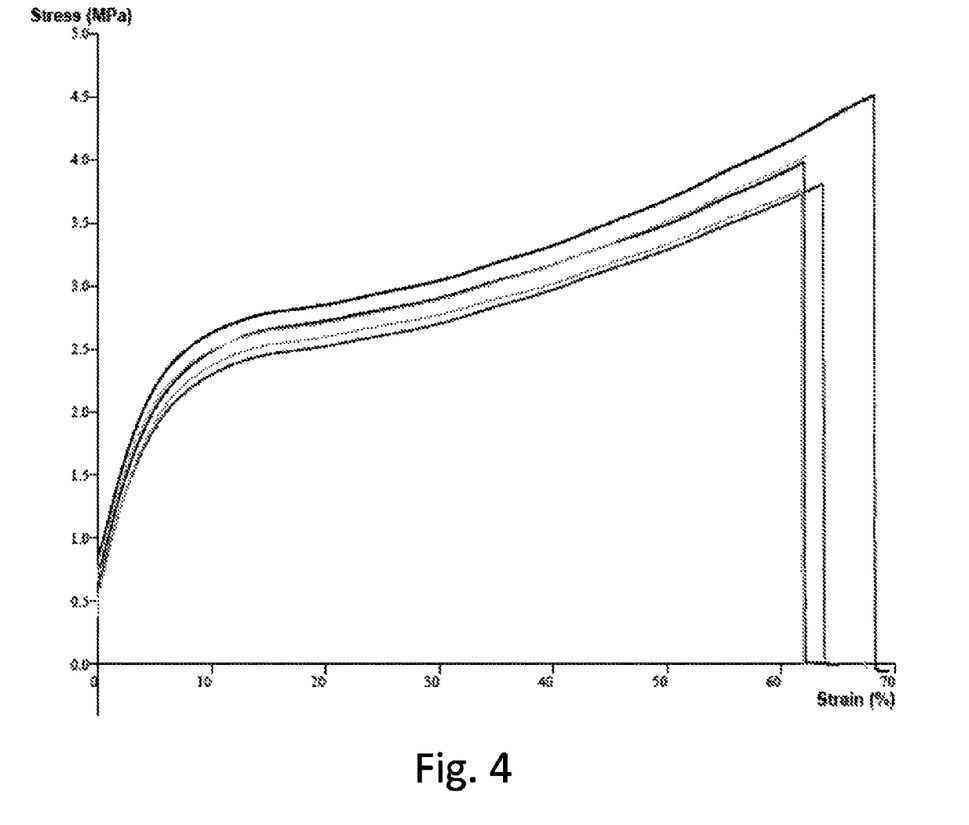
FIG. 4 is a graph showing stress-strain curves of a polymer film comprising high molecular weight $\varnothing(PIB-CA)_3$ (MW=6500 g/mol), low molecular weight $\varnothing(PIB-CA)_3$ (MW=3000 g/mol), and Oct-CA recorded in triplicate. The curves are identical within experimental error.

A well-dried 10 mL vial was charged with high molecular weight Ø(PIB-CA)$_3$ (0.354 g, MW=6500 g/mol), low molecular weight Ø(PIB-CA)$_3$ (1.442 g, MW=3000 g/mol), and Oct-CA (5,2089 g). The mixture formed a single slightly hazy phase, which persisted for a week at RT. Films comprising 5% High-Ø(PIB-CA)$_3$ (MW 6500 g/mol), 21% Low-Ø(PIB-CA)$_3$ (MW 3000 g/mol) and 74% Oct-CA were prepared and their static mechanical properties were determined. Films were prepared by vigorously manually agitating the solution for 1-2 seconds and rapidly pouring it into a 7×7 cm Teflon mold, allowing the volatiles to evaporate in a fume hood for 1 h, and drying the film at 35° C. to constant weight (for 15 hrs). 2 mL diethyl-ether/1.4835 g adhesives and 100 μL TWEEN 20 (containing 0.64 mM DABCO) were used to make the films. The stress-strain curves of this polymer film were recorded in 5 tests and are shown in FIG. 4. The curves are identical within experimental error. The ultimate tensile strength was ~4.1 MPa and the strain at break was ~65%. (See FIG. 4).

In light of the foregoing, it should be appreciated that the present invention significantly advances the art by providing a liquid adhesive composition and polymer co-network that are structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A substantially homogeneous liquid adhesive composition useful for wound closure and skin protection comprising:
    a first cyanoacrylate tri-telechelic star polymer comprising polyisobutylene terminated with cyanoacrylate groups and having a high number average molecular weight of from about 6,000 g/mole to about 10,000 g/mole;
    2-octyl cyanoacrylate; and
    a second cyanoacrylate tri-telechelic star polymer comprising polyisobutylene terminated with cyanoacrylate groups and having a low number average molecular weight of from about 1,000 g/mole to about 4,000 g/mole.

2. The substantially homogeneous liquid adhesive composition of claim 1 wherein said homogeneous liquid adhesive composition does not contain a solvent.

3. The substantially homogeneous liquid adhesive composition of claim 1 wherein said first cyanoacrylate tri-telechelic star polymer has a number average molecular weight of about 6,500 g/mole.

4. The substantially homogeneous liquid adhesive composition of claim 1 wherein said second cyanoacrylate tri-telechelic star polymer has a number average molecular weight of about 3,000 g/mole.

5. The substantially homogeneous liquid adhesive composition of claim 1 wherein said first cyanoacrylate tri-telechelic star polymer comprises from about 0.1% by weight to about 10% by weight of said homogeneous liquid adhesive composition; said 2-octyl cyanoacrylate comprises from about 50% by weight to about 75% by weight of said homogeneous liquid adhesive composition; and said second cyanoacrylate tri-telechelic star polymer comprises from about 20% by weight to about 40% by weight of said homogeneous liquid adhesive composition.

6. The substantially homogeneous liquid adhesive composition of claim 1 wherein the ratio of said first cyanoacrylate tri-telechelic star polymer to said second tri-cyanoacrylate telechelic star polymer is at least about 1:3 by weight.

7. A polymer co-network useful for wound closure and skin protection comprising:
   the residue of a first cyanoacrylate tri-telechelic star polymer, wherein said first cyanoacrylate tri-telechelic star polymer comprises polyisobutylene terminated with cyanoacrylate groups and has a number average molecular weight of from about 6,000 g/mole to about 10,000 g/mole;
   the residue of 2-octyl cyanoacrylate; and
   the residue of a second cyanoacrylate tri-telechelic star polymer, wherein said second cyanoacrylate tri-telechelic star polymer comprises polyisobutylene terminated with cyanoacrylate groups and has a number average molecular weight of from about 1,000 g/mole to about 4,000 g/mole.

8. The polymer co-network of claim 7 wherein said first cyanoacrylate tri-telechelic star polymer has a number average molecular weight of about 6,500 g/mole.

9. The polymer co-network of claim 7 wherein said second cyanoacrylate tri-telechelic star polymer has a number average molecular weight of about 3,000 g/mole.

10. The polymer co-network of claim 7 having a tensile strength of from about 3 MPa to about 6 MPa.

11. The polymer co-network of claim 7 having a tensile elongation of from about 60% to about 70%.

12. The polymer co-network of claim 7, wherein said first cyanoacrylate tri-telechelic star polymer comprises from about 0.1% by weight to about 10% by weight of said polymer co-network; said 2-octyl cyanoacrylate comprises from about 50% by weight to about 75% by weight of said polymer co-network; and said second cyanoacrylate tri-telechelic star polymer comprises from about 20% by weight to about 40% by weight of said polymer co-network.

13. The polymer co-network of claim 7 wherein the ratio of the residue of said first cyanoacrylate tri-telechelic star polymer to the residue of said second cyanoacrylate tri-telechelic star polymer is at least about 1:3.

14. A polymer co-network useful for wound closure and skin protection comprising the reaction product of:
   a first cyanoacrylate tri-telechelic star polymer comprising polyisobutylene terminated with cyanoacrylate groups and having a high number average molecular weight of from about 6,000 g/mole to about 10,000 g/mole;
   2-octo cyanoacrylate;
   a second cyanoacrylate tri-telechelic star polymer comprising polyisobutylene terminated with cyanoacrylate groups and having a low number average molecular weight of from about 1,000 g/mole to about 4,000 g/mole; and
   a nucleophile.

15. The polymer co-network of claim 14 wherein said first cyanoacrylate tri-telechelic star polymer has a number average molecular weight of about 6,500 g/mole.

16. The polymer co-network of claim 14 wherein said second cyanoacrylate tri-telechelic star polymer has a number average molecular weight of about 3,000 g/mole.

17. The polymer co-network of claim 14 having a tensile strength of from about 3 MPa to about 6 MPa.

18. The polymer co-network of claim 14 having a tensile elongation of from about 60% to about 70%.

19. The polymer co-network of claim 14, wherein said first cyanoacrylate tri-telechelic star polymer comprises from about 0.1% by weight to about 10% by weight of said polymer co-network; said 2-octyl cyanoacrylate comprises from about 50% by weight to about 75% by weight of said polymer co-network; and said second cyanoacrylate tri-telechelic star polymer comprises from about 20% by weight to about 40% by weight of said polymer co-network.

20. The polymer co-network of claim 14 wherein the ratio of the said first cyanoacrylate tri-telechelic star polymer to of said second cyanoacrylate tri-telechelic star polymer is from about 1:3 to about 1:6 by weight.

21. A method for forming a homogeneous polymer co-network useful for wound closure and skin protection comprising:
   A. preparing a substantially homogeneous liquid adhesive composition comprising:
      a first cyanoacrylate tri-telechelic star polymer comprising polyisobutylene terminated with cyanoacrylate groups and having a number average molecular weight of from 6,000 g/mole to about 10,000 g/mole;
      2-octyl cyanoacrylate; and
      a second cyanoacrylate tri-telechelic star polymer comprising polyisobutylene terminated with cyanoacrylate groups and having a number average molecular weight of from about 1,000 g/mole to about 4,000 g/mole;
   B. applying said substantially homogeneous liquid adhesive composition to a tissue having one or more available nucleophiles, wherein said nucleophiles cause said homogeneous liquid adhesive composition to co-polymerize to form a homogeneous polymer co-network comprising the residues of said first cyanoacrylate tri-telechelic star polymer, said second cyanoacrylate tri-telechelic star polymer, and said 2-octyl cyanoacrylate.

22. The method of claim 21, wherein said first cyanoacrylate tri-telechelic star polymer comprises from about 0.1% by weight to about 10% by weight of said substantially homogeneous liquid adhesive composition; said 2-octyl cyanoacrylate comprises from about 50% by weight to about 75% by weight of said substantially homogeneous liquid adhesive composition; and said second cyanoacrylate tri-telechelic star polymer comprises from about 20% by weight to about 40% by weight of said substantially homogeneous liquid adhesive composition.

23. The method of claim 21 wherein the ratio of said first tri-telechelic star polymer to said second tri-telechelic star polymer in said substantially homogeneous liquid adhesive composition is from about 1:3 to about 1:6 by weight.

* * * * *